United States Patent [19]
Burnett

[11] Patent Number: 5,007,895
[45] Date of Patent: Apr. 16, 1991

[54] WOUND PACKING INSTRUMENT

[76] Inventor: George S. Burnett, 935 Gossett Rd., Spartanburg, S.C. 29302

[21] Appl. No.: 333,338

[22] Filed: Apr. 5, 1989

[51] Int. Cl.$^5$ ............................................. A61F 13/20
[52] U.S. Cl. ................................... 604/11; 604/13
[58] Field of Search ................................. 604/11-14

[56] References Cited

U.S. PATENT DOCUMENTS

| | | | |
|---|---|---|---|
| 636,637 | 11/1899 | Cooke | 604/13 |
| 654,564 | 7/1900 | Dargatz | 604/13 |
| 682,090 | 9/1901 | Lee | 604/13 |
| 702,997 | 6/1902 | Pugh | 604/13 |
| 1,456,828 | 5/1923 | Pistor | 604/13 |
| 1,473,062 | 11/1923 | Tinker | 604/13 |
| 1,562,656 | 11/1925 | Park | 604/13 |
| 2,524,195 | 4/1950 | Hoover | 604/13 |

Primary Examiner—Stephen C. Pellegrino
Assistant Examiner—Michael Rafa
Attorney, Agent, or Firm—Dority & Manning

[57] ABSTRACT

An instrument for packing wounds with gauze or the like is provided having an elongated shaft, a rounded tip at a distal end of the shaft, a notch within the tip with the notch bieng sufficiently narrow to grip the gauze yet wide enough to prevent the gauze from being pulled from the wound when the probe is pulled from the wound. The shaft and tip may be hollow to allow for flushing and aspirating of the wound, and a cutting blade may be provided along the shaft to sever the material at a desired length.

22 Claims, 2 Drawing Sheets

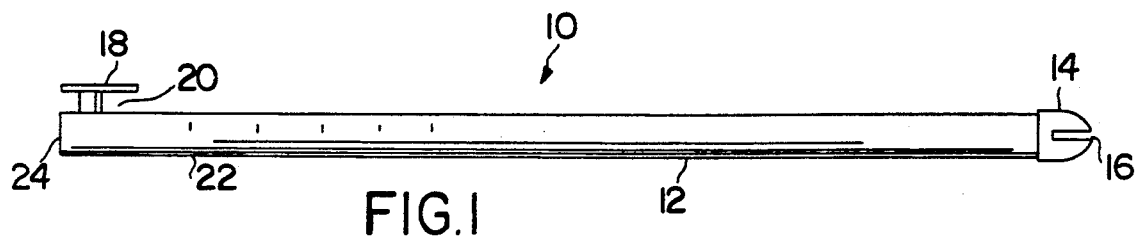
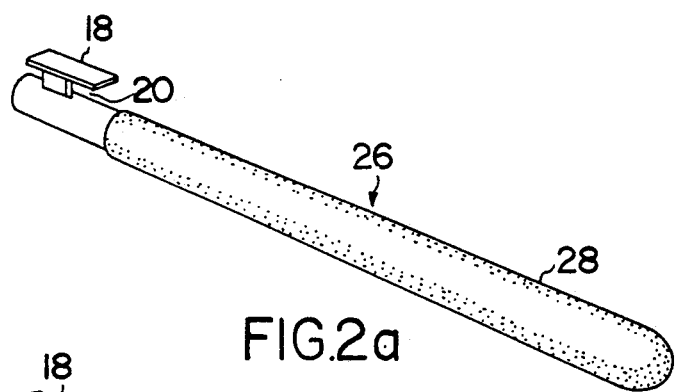
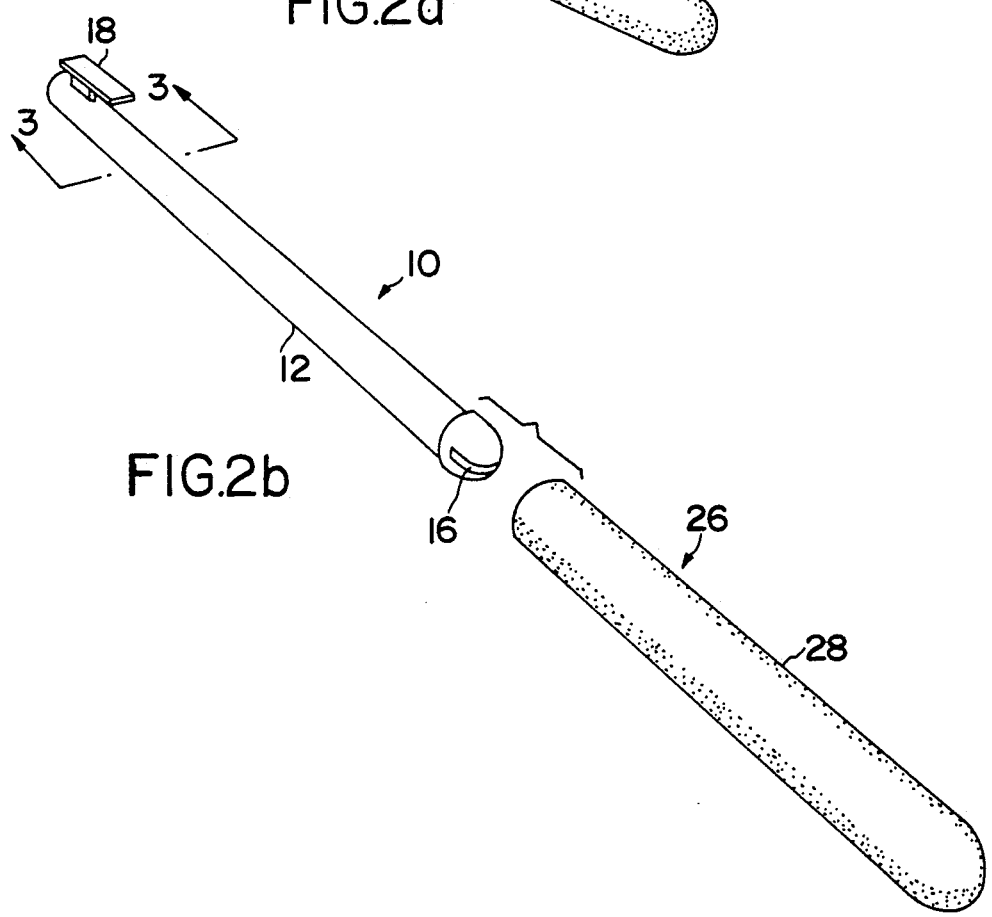
FIG.1
FIG.2a
FIG.2b

WOUND PACKING INSTRUMENT

BACKGROUND OF THE INVENTION

Generally wounds are packed with gauze using forceps or tweezers. The nurse or doctor uses scissors to cut a length of gauze from a roll and forceps to pack the gauze into the wound. The process can be cumbersome and the relative inflexibility of forceps can cause discomfort to the patient. Moreover, often the gauze is not properly placed in the bottom of the wound, leading to the possibility of less than proper healing.

Alternative devices have been provided for dressing wounds generally comprised of elongated hollow shafts and means for pushing gauze through the shafts into a wound. Examples of such wound packers are found in U.S. Pat. Nos. 636,637 and 682,090.

However, there has been no apparatus provided which can be used to properly treat and measure a wound, particularly a deep wound, and to properly cut and pack gauze into the wound.

SUMMARY OF THE INVENTION

It is thus an object of the present invention to provide an instrument for packing wounds with gauze.

It is a further object of the present invention to provide a compact instrument contoured for atraumatic contact with the wound for properly packing gauze and further treating the wound.

These as well as other objects are accomplished by providing an instrument having an elongated shaft capable of sterilization, a tip at a distal end of the shaft designed for atraumatic contact with the wound, the tip having means for holding a portion of material to be inserted into the wound, with that means being adapted to hold the material during insertion into the wound while permitting ready release of the material for withdrawal of the instrument from the wound.

More particularly, wound packing instruments, according to the present invention, are preferably molded of polymeric materials with a distal tip of same defining a smooth, rounded tip for avoiding any appreciable trauma to a wound surface during insertion of a packing material such as a sterile gauze thereinto, and at the same time, once the material is properly inserted, permitting withdrawal of the instrument while leaving the inserted material in place.

In a most preferred embodiment, a device according to the present invention further includes means away from the distal end for severing a material to be inserted.

DETAILED DESCRIPTION OF THE DRAWINGS

FIG. 1 is a side view of an instrument in accordance with the present invention.

FIG. 2a is a perspective view of an instrument in accordance with the present invention having a roughened covering thereon.

FIG. 2b is a perspective view of an instrument in accordance with the present invention in linear alignment with a roughened cover.

DESCRIPTION OF A PREFERRED EMBODIMENT

Referring to FIG. 1 of the drawings, an instrument 10, according to teachings of the present invention, is disclosed and includes an elongated shaft 12 having a tip 14 at a distal end thereof. Tip 14 has a means such as notch 16 for holding a portion of gauze or other material for insertion into a wound. The means for holding the material is necessarily adapted to hold the material during insertion into a wound while permitting release of the material for withdrawal of instrument 10 from the wound, leaving the packing material properly within the wound. Thus, while notch 16 holds the gauze to tip 14, it does not do so with a gripping action. Rather, the gauze is held to the shaft 12 by the user, thereby allowing for release of the material for withdrawal of the instrument from the wound. Although notch 16 is the preferred means for holding the material, it is to be understood that other means such as a forwardly extending hook may be employed. Tip 14 is preferably molded into a rounded semisphere for atraumatic contact with the wound. The elongated shaft 12 is preferably relatively flexible to further reduce trauma to the wound.

Figure 3:
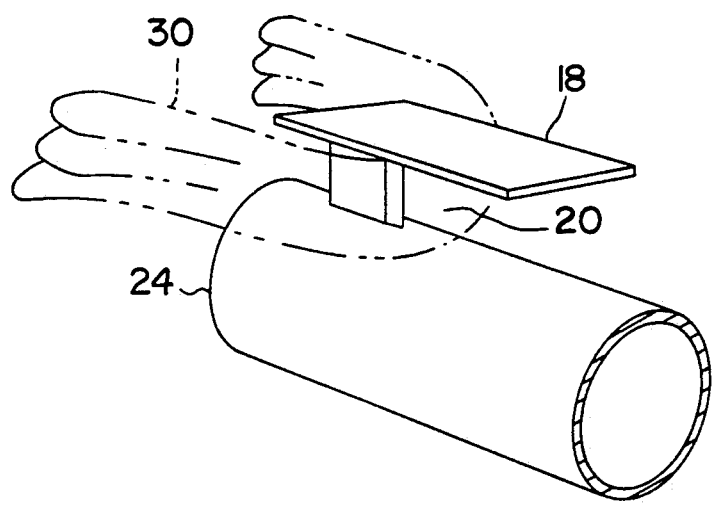
FIG. 3 is a view taken along the line 3—3 of FIG. 1 illustrating the shielded blade of the present invention.

Preferably a means is carried at the proximal end of shaft 12 for securing the gauze or other material from a container. A U-shaped or rectangular shaped member of hook 18 is shown in the embodiment of FIG. 1 for accomplishing this task. Means for cutting the material such as shielded blade 20 may be provided within the U-shaped member allowing the user to cut the gauze or other material with one instrument and, if need be, with one hand, avoiding the use of scissors, forceps and the like. Shielding of the blade within the means for securing material is best illustrated in FIG. 3 which is a view taken along the line 3—3 of FIG. 1 looking from a distal end of the instrument toward the proximal end. Blade 20 presents an exemplary cutting edge for gauze which is shielded from the user as well as the wound. Gauze 30 withdrawn from a container by member 18 need only be drawn along the length of elongated shaft 12 toward the proximal end for cutting by blade 20. Additionally, indicia such as shown in FIG. 1 at 22 may be provided along the length of shaft 12 for measuring the depth as well as the width and length of the wound.

Elongated shaft 12 may also be hollow as depicted in FIG. 3, thereby allowing for fluid communication throughout the instrument from the proximal to the distal end. Opening 24 at proximal end of the shaft accommodates the male end of a syringe, squeeze bottle or IV tubing permitting irrigation and aspiration of the wound; that is, antiseptic fluid may be introduced to the bottom of the wound through the instrument and drainage may be withdrawn.

FIG. 2 shows an elongated covering 26 for shielding the instrument having a roughened outer surface 28 thereon. Covering 26 may be made of fabric, a hard plastic or the like, but should present a roughened outer surface for debridement of the wound, that is, removal of dead tissue from the inner walls of the wound. Covering 26 should also preferably extend far enough up the instrument to allow a hand gripping the instrument to also grip the cover. It may be further secured to the instrument as with an elastic band.

Figure 4:
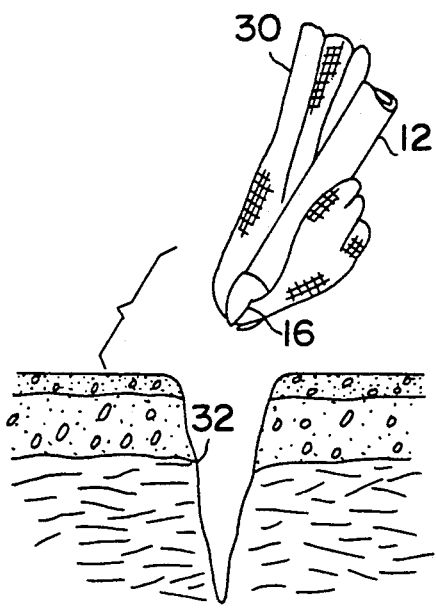
FIG. 4 is a perspective view of the instrument of the present invention in use.
Figure 5:
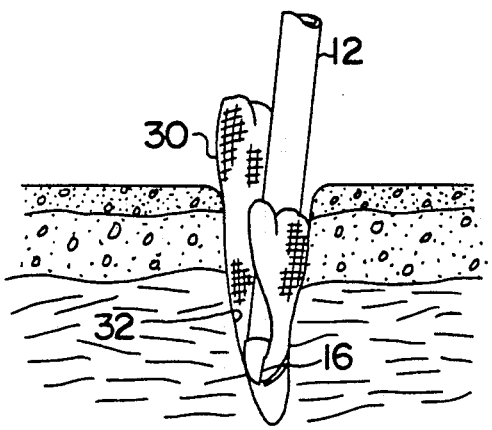
FIG. 5 is a perspective view of the instrument of the present invention in use.
Figure 6:
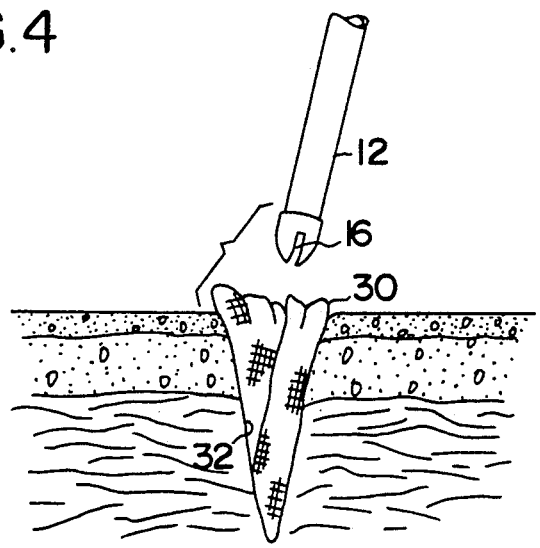
FIG. 6 is a perspective view of the instrument of the present invention in use.

Thus, the operation of the instrument of this invention may involve any or all of the following steps. These steps include: debridement of dead tissue within the wound using covering 26 or the like, aspirating the wound by withdrawing drainage up through the instrument, flushing and cleaning of the wound by introducing antiseptic fluid into the wound through the instrument, measuring of the wound with the indicia along the shaft of the instrument, securement of a length of gauze or other wound packing material from a roll or container using U-shaped member 18, cutting the gauze with a shielded blade 20 within U-shaped member 18, and packing the wound with gauze as is shown in FIGS. 4 through 6. FIGS. 4 through 6 illustrate gauze 30 guided by notch 16 being progressively packed into the recess of a wound 32. As is evident from these figures, the means for holding the material, such as notch 16, must be adapted to guide the gauze during insertion of the instrument into the wound while permitting withdrawal of the instrument from the wound without pulling the gauze back out of the wound.

Thus, an instrument is provided for packing material such as gauze into wounds which additionally in certain embodiments may be used to flush, aspirate, debride and/or measure the wound. The device is especially suited for the packing of deep, narrow wounds and can be modified for packing very narrow wounds by providing a narrow, short probe tip while a remainder of the shaft proximal to the tip is provided at a larger diameter to allow for better control. The instrument of this invention is preferably constructed from a sterilizable polymer and may be molded and of unitary construction or assembled.

The embodiments discussed herein and portions thereof may be interchangeably used with all of the wound packing instruments according to the present invention.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not limitative of the invention so further described in such appended claims.

That which is claimed is:

1. An instrument for placing a material into a wound, comprising:
   an elongated shaft being capable of sterilization;
   a tip at a distal end of said shaft adapted for atraumatic contact with the wound;
   said tip having means for holding a portion of material to be inserted into the wound; and
   said means for holding being configured to hold the material during insertion into the wound and permitting release of the material for withdrawal of the instrument from the wound;
   wherein said instrument is of one piece construction.

2. The instrument as set forth in claim 1 wherein the elongated shaft is flexible.

3. The instrument as set forth in claim 1 wherein the elongated shaft is hollow permitting the passage of fluid through the instrument to and from the wound.

4. The instrument as set forth in claim 1 wherein the tip is rounded for atraumatic contact with the wound.

5. The instrument as set forth in claim 1 wherein the means for holding a portion of material is a notch defined within said tip sized to hold the material during insertion into the wound and permitting release of the material for withdrawal of the instrument from the wound.

6. The instrument as set forth in claim 1 further including a means for securing the material to be inserted into the wound.

7. The instrument as set forth in claim 6 further including a shielded cutter means within said means for securing said material.

8. The instrument as set forth in claim 1 further including an elongated covering for the shaft having a roughened outer surface for debridement of the wound.

9. The instrument as set forth in claim 1 further including indicia along the shaft for measuring the wound.

10. An instrument as set forth in claim 1, wherein said elongated shaft is polymeric.

11. An instrument for placing a packing material into a wound, comprising:
    an elongated shaft capable of sterilization;
    cutting means located on said instrument for cutting the material;
    a tip at a distal end of the shaft for atraumatic contact with the wound;
    said tip having means for holding a portion of material to be inserted into the wound; and
    said means for holding being configured to hold the material during insertion into the wound and permitting release of the material for withdrawal of the instrument from the wound.

12. The instrument set forth in claim 11 further comprising means at a proximal end of the shaft for securing the material to be inserted into the wound.

13. The instrument set forth in claim 12 wherein the means for securing the material is a rectangular shaped member.

14. The instrument set forth in claim 13 wherein the means for cutting the material is a blade shielded by the rectangular shaped member.

15. The instrument set forth in claim 11 wherein the elongated shaft is flexible.

16. The instrument set forth in claim 11 wherein the elongated shaft is hollow permitting the passage of fluid through the instrument to and from the wound.

17. The instrument set forth in claim 11 wherein the means for holding a portion of material is a notch defined within said tip.

18. The instrument stet forth in claim 11 further including an elongated covering for the shaft having a roughened outer surface for debridement of the wound.

19. The instrument set forth in claim 11 further including indicia along the shaft for measuring the wound.

20. An instrument as set forth in claim 17, wherein the elongated shaft is polymeric.

21. A flexible instrument for placing a material into a wound, comprising:
    a hollow elongated shaft being capable of sterilization;
    indicia along the elongated shaft for measuring the wound;
    a rectangular shaped member at a proximal end of the shaft for securing the material to be inserted into the wound;

a blade shielded by said rectangular shaped member for cutting the material;

a tip at a distal end of the shaft rounded for atraumatic contact with the wound;

said tip having a notch for holding a portion of material to be inserted into the wound;

said notch being sized to hold the material during insertion into the wound and permitting release of the material for withdrawal of the instrument from the wound.

22. The instrument set forth in claim 21 further including an elongated covering mountable at the distal end of the shaft having a roughened outer surface for debridement of the wound.

* * * * *

UNITED STATES PATENT AND TRADEMARK OFFICE
CERTIFICATE OF CORRECTION

PATENT NO. : 5,007,895
DATED : April 16, 1991
INVENTOR(S) : George S. Burnett

It is certified that error appears in the above-identified patent and that said Letters Patent is hereby corrected as shown below:

In column 2, line 34, change "of hook 18" to --or hook 18--.

Column 4, line 52:

In claim 18, line 1, change "The instrument stet forth" to --The instrument set forth--.

Column 4, line 58:
In claim 20, line 1, change "in claim 17" to --in claim 11--.

Signed and Sealed this

Eleventh Day of August, 1992

Attest:

DOUGLAS B. COMER

*Attesting Officer*      *Acting Commissioner of Patents and Trademarks*